United States Patent
Whisler et al.

(10) Patent No.: US 11,241,215 B2
(45) Date of Patent: Feb. 8, 2022

(54) MEMBRANE FOR BREAST ULTRASOUND SYSTEMS

(71) Applicant: General Electric Company, Schenectady, NY (US)

(72) Inventors: Doug Whisler, Seattle, WA (US); Bruce Brogden, Pleasanton, CA (US); Ross Stalter, Hartland, WI (US)

(73) Assignee: General Electric Company, Schenectady, NY (US)

( * ) Notice: Subject to any disclaimer, the term of this patent is extended or adjusted under 35 U.S.C. 154(b) by 1110 days.

(21) Appl. No.: 15/796,050

(22) Filed: Oct. 27, 2017

(65) Prior Publication Data

US 2019/0125304 A1 May 2, 2019

(51) Int. Cl.
*A61B 8/00* (2006.01)
*A61B 8/08* (2006.01)

(52) U.S. Cl.
CPC .......... *A61B 8/4272* (2013.01); *A61B 8/0825* (2013.01); *A61B 8/403* (2013.01); *A61B 8/4209* (2013.01); *A61B 8/4405* (2013.01)

(58) Field of Classification Search
CPC ... A61B 8/4272; A61B 8/4494; A61B 8/4405; A61B 8/461; A61B 8/0825; A61B 6/502; A61B 5/43; A61B 5/4306; A61B 5/4312
USPC ................ 600/459, 407, 437, 443, 445, 447
See application file for complete search history.

(56) References Cited

U.S. PATENT DOCUMENTS

| | | | | |
|---|---|---|---|---|
| 3,964,296 | A * | 6/1976 | Matzuk | A61B 8/00 73/607 |
| 4,347,850 | A * | 9/1982 | Kelly-Fry | A61B 8/0825 128/915 |
| 4,662,375 | A * | 5/1987 | Hepp | A61B 17/225 601/4 |
| 6,027,457 | A * | 2/2000 | Shmulewitz | A61B 8/0833 600/437 |
| 9,597,056 | B2 | 3/2017 | Summers et al. | |
| 2005/0080333 | A1* | 4/2005 | Piron | A61B 8/0825 600/417 |
| 2005/0113683 | A1* | 5/2005 | Lokhandwalla | A61B 6/0414 600/427 |
| 2008/0004526 | A1* | 1/2008 | Gross | A61B 90/17 600/437 |
| 2008/0033292 | A1* | 2/2008 | Shafran | A61B 8/44 600/437 |

(Continued)

FOREIGN PATENT DOCUMENTS

DE 3227624 A1 * 1/1984 ........... A61B 8/0825

OTHER PUBLICATIONS

DE 3227624 A1 (Siemens AG). Translated by Espacenet. Jan. 26, 1984 [retrieved on Jan. 29, 2021].*

*Primary Examiner* — Carolyn A Pehlke
*Assistant Examiner* — Victoria Fang
(74) *Attorney, Agent, or Firm* — McCoy Russell LLP

(57) ABSTRACT

Various embodiments of a breast ultrasound scanning apparatus are provided. In one embodiment, a system comprises an imaging assembly comprising an ultrasound transducer, a frame housing the imaging assembly, and a membrane directly and removably coupled to the frame. In this way, the cost of performing an ultrasound scan with the imaging assembly may be reduced while the comfort for a patient being scanned with the imaging assembly is increased.

16 Claims, 8 Drawing Sheets

(56) References Cited

U.S. PATENT DOCUMENTS

| | | | | |
|---|---|---|---|---|
| 2008/0194959 A1* | 8/2008 | Wang | ............... | A61B 8/54 600/445 |
| 2010/0063396 A1* | 3/2010 | Anderson | ............... | A61B 8/462 600/459 |
| 2012/0291776 A1* | 11/2012 | Van Der Mark | .... | A61M 11/005 128/200.14 |
| 2013/0184602 A1* | 7/2013 | Brambilla | ............... | A61M 16/201 600/543 |
| 2015/0094588 A1* | 4/2015 | Summers | ............... | A61B 8/4218 600/445 |
| 2015/0265243 A1* | 9/2015 | Kelly | ............... | A61B 8/4218 600/443 |
| 2016/0128670 A1* | 5/2016 | Morgan | ............... | A61B 8/4281 600/472 |
| 2019/0328357 A1* | 10/2019 | Cermak | ............... | C09J 183/00 |

* cited by examiner

MEMBRANE FOR BREAST ULTRASOUND SYSTEMS

FIELD

Embodiments of the subject matter disclosed herein relate to non-invasive medical imaging, and more particularly, to a membrane for a breast ultrasound scanning apparatus.

BACKGROUND

Volumetric ultrasound scanning of the breast may be used as a complementary modality for breast cancer screening. Volumetric ultrasound scanning usually involves the movement of an ultrasound transducer relative to a tissue sample and the processing of resultant ultrasound echoes to form a data volume representing at least one acoustic property of the tissue sample. Whereas a conventional two-dimensional x-ray mammogram only detects a summation of the x-ray opacity of individual slices of breast tissue over the entire breast, ultrasound can separately detect the sonographic properties of individual slices of breast tissue, and therefore may allow detection of breast lesions where x-ray mammography alone fails. Further, volumetric ultrasound offers advantages over x-ray mammography in patients with dense breast tissue (e.g., high content of fibroglandular tissues). Thus, the use of volumetric ultrasound scanning in conjunction with conventional x-ray mammography may increase the early breast cancer detection rate.

In one example, a full-field breast ultrasound (FFBU) scanning apparatus may be used to image breast tissue in one or more planes. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast. Prior to initiating the scanning, a user of the scanning apparatus may place the ultrasound transducer on the patient tissue and apply a downward force on the transducer to compress the tissue in order to properly image the tissue. The membrane is permanently fixed to a hard-shell frame that attaches to the scanning apparatus, and is intended to be disposed after scanning the tissue of a patient. However, the cost of the membrane with a hard-shell frame may be prohibitive for such single-use. Further, the compression of the tissue against the plastic frame is often painful or uncomfortable for the patient.

BRIEF DESCRIPTION

In one embodiment, a system comprises an imaging assembly comprising an ultrasound transducer, a frame housing the imaging assembly, and a membrane directly and removably coupled to the frame. In this way, the cost of performing a scan with the imaging assembly may be reduced while the comfort for a patient being scanned with the imaging assembly is increased.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
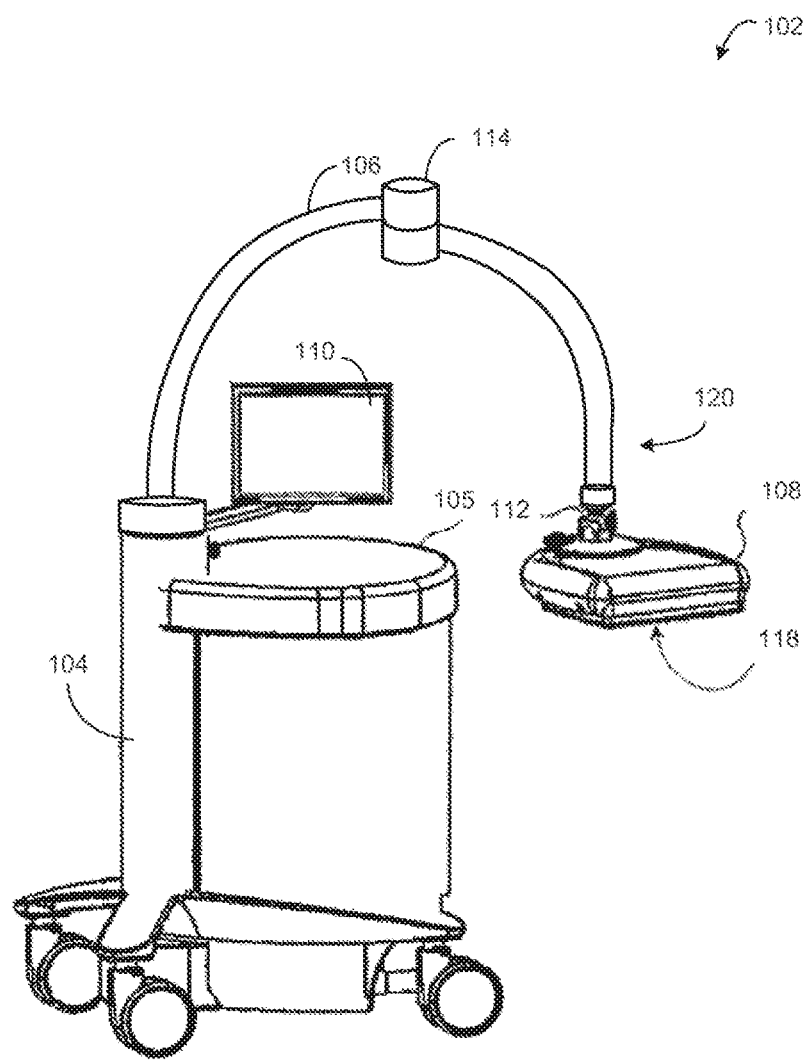
FIG. 1 shows a perspective view of a scanning apparatus according to an embodiment.
Figure 2:
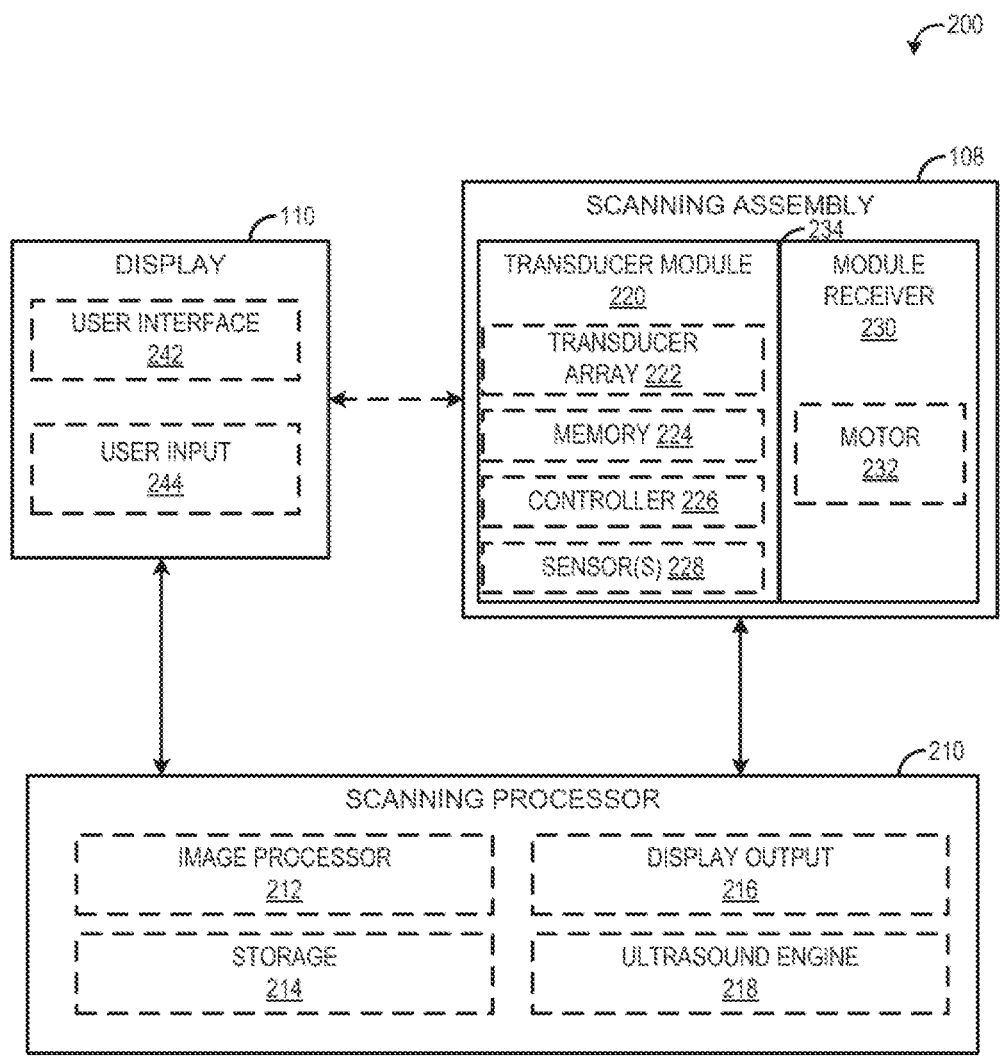
FIG. 2 shows a block schematic diagram of various system components of a scanning apparatus according to an embodiment.
Figure 3:
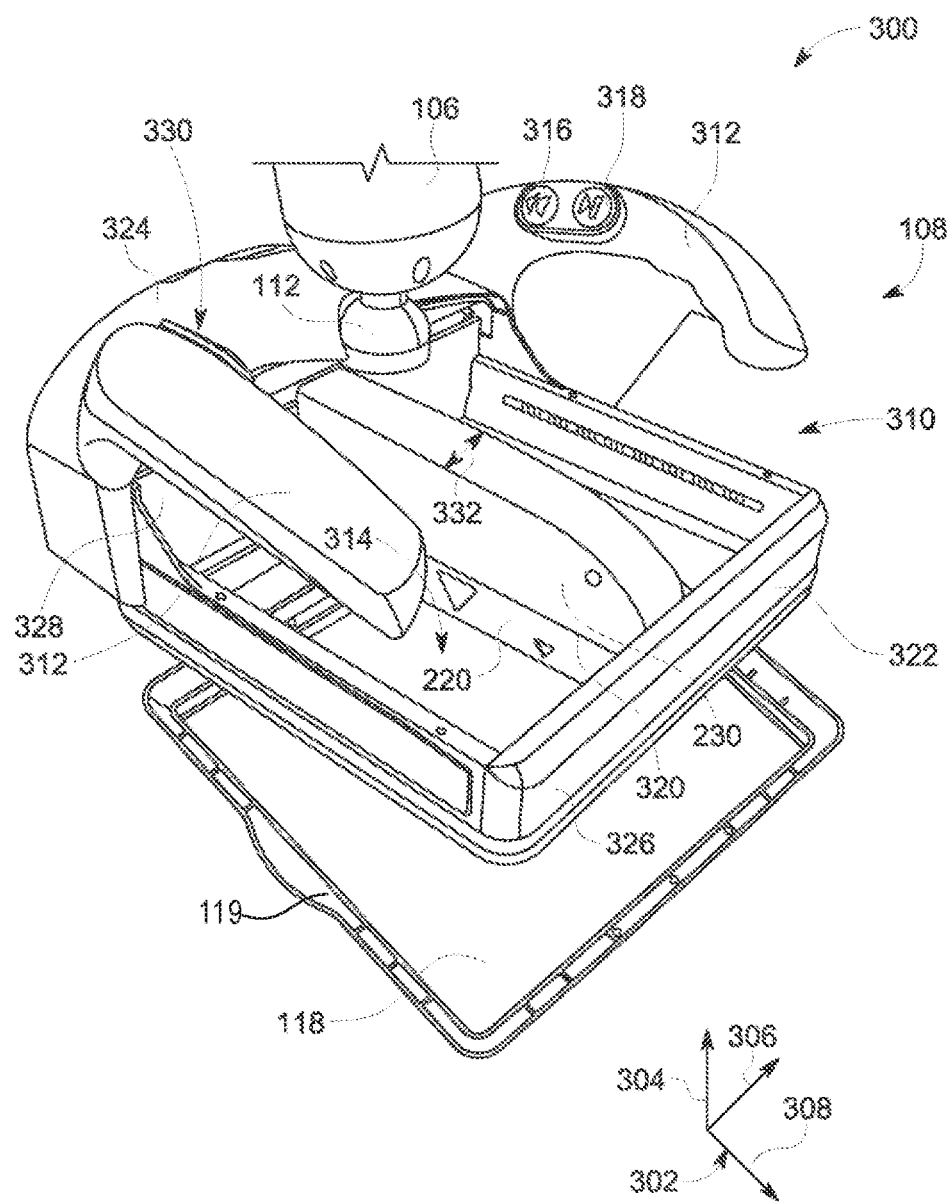
FIG. 3 shows a scanning assembly of a scanning apparatus according to an embodiment.
Figure 4:
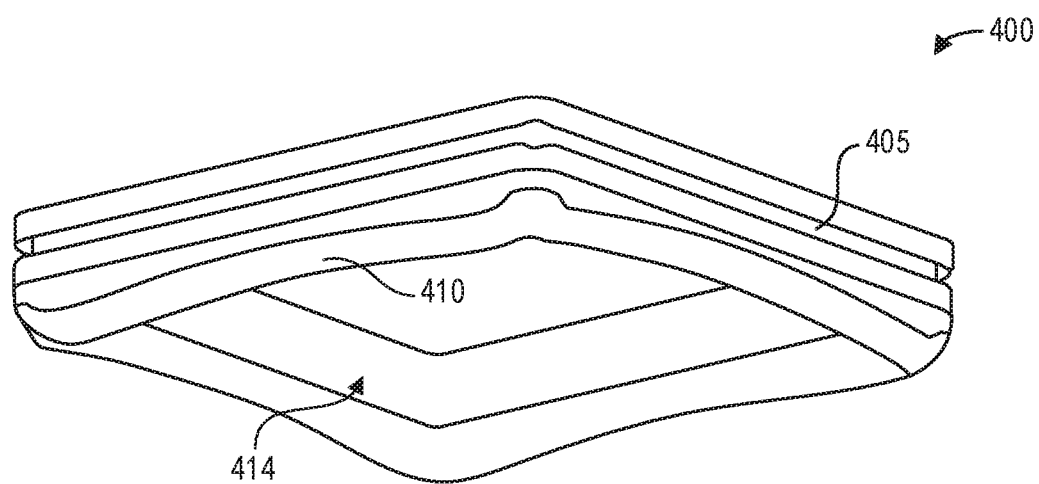
FIG. 4 shows a perspective view of a lower surface of a scanning assembly of a scanning apparatus according to an embodiment.
Figure 5:
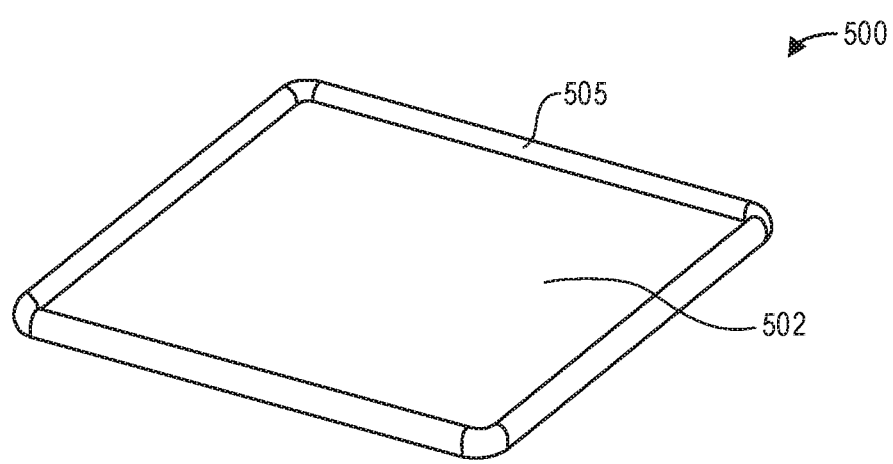
FIG. 5 shows a perspective view of a membrane for a scanning assembly according to an embodiment.
Figure 6:
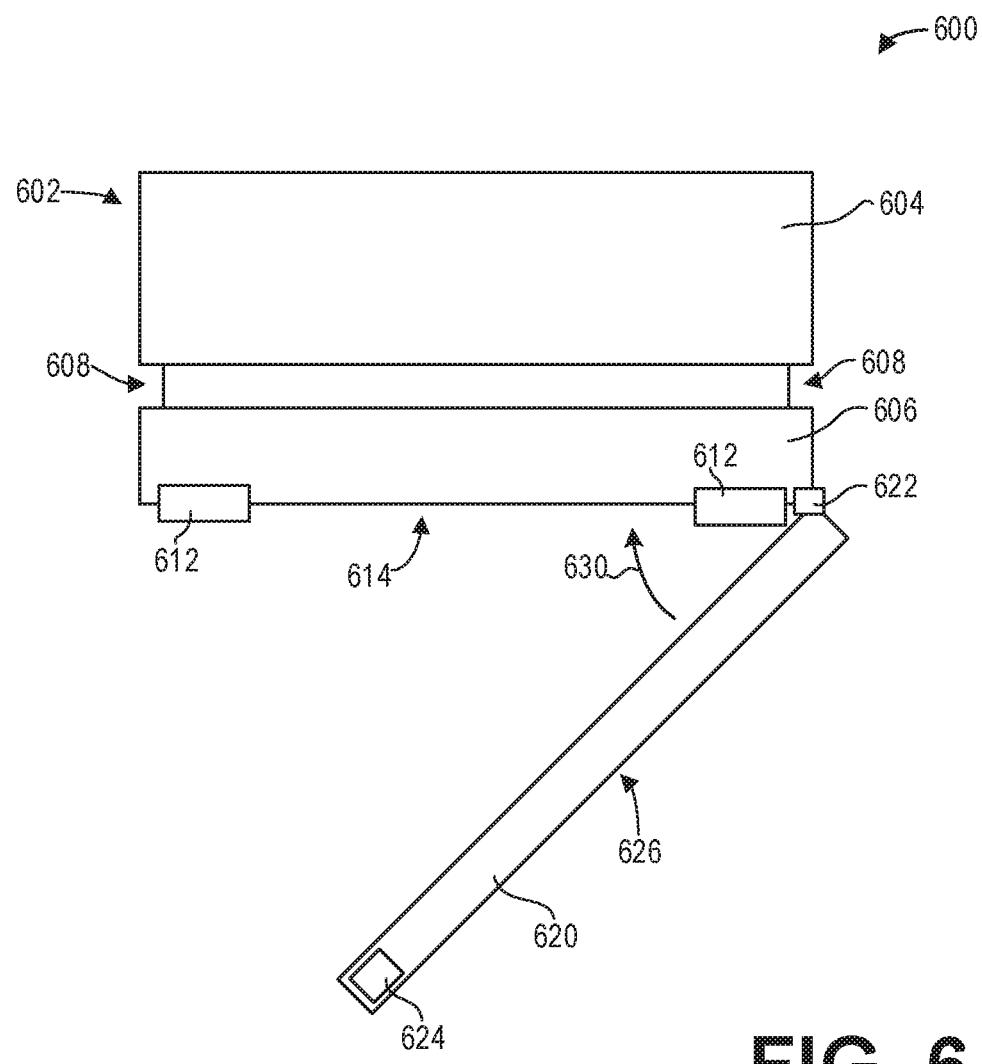
FIG. 6 shows a block diagram illustrating a scanning assembly of a scanning apparatus according to an embodiment.
Figure 7:
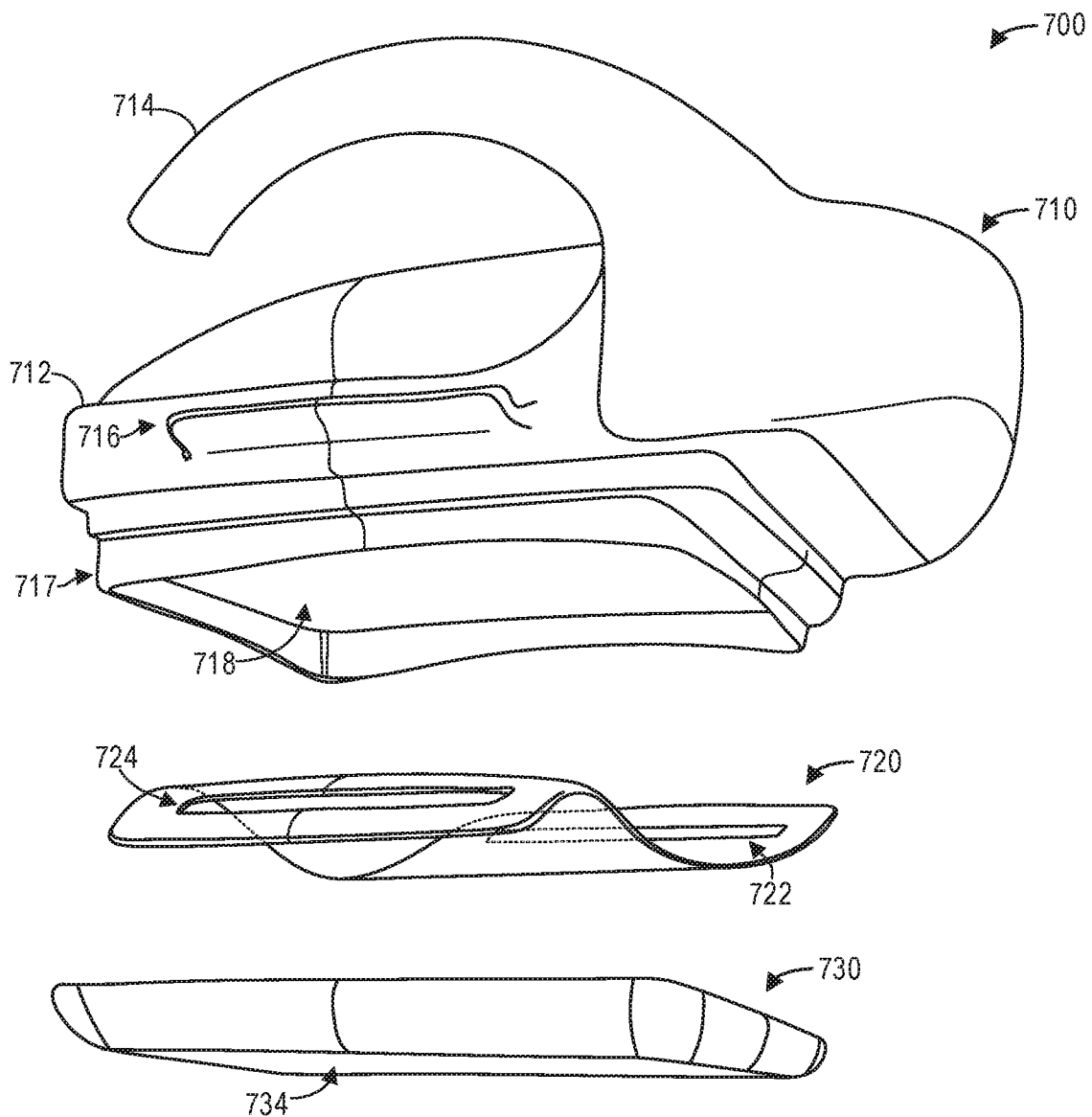
FIG. 7 shows a perspective exploded view of a scanning assembly for a scanning apparatus according to an embodiment.
Figure 8:
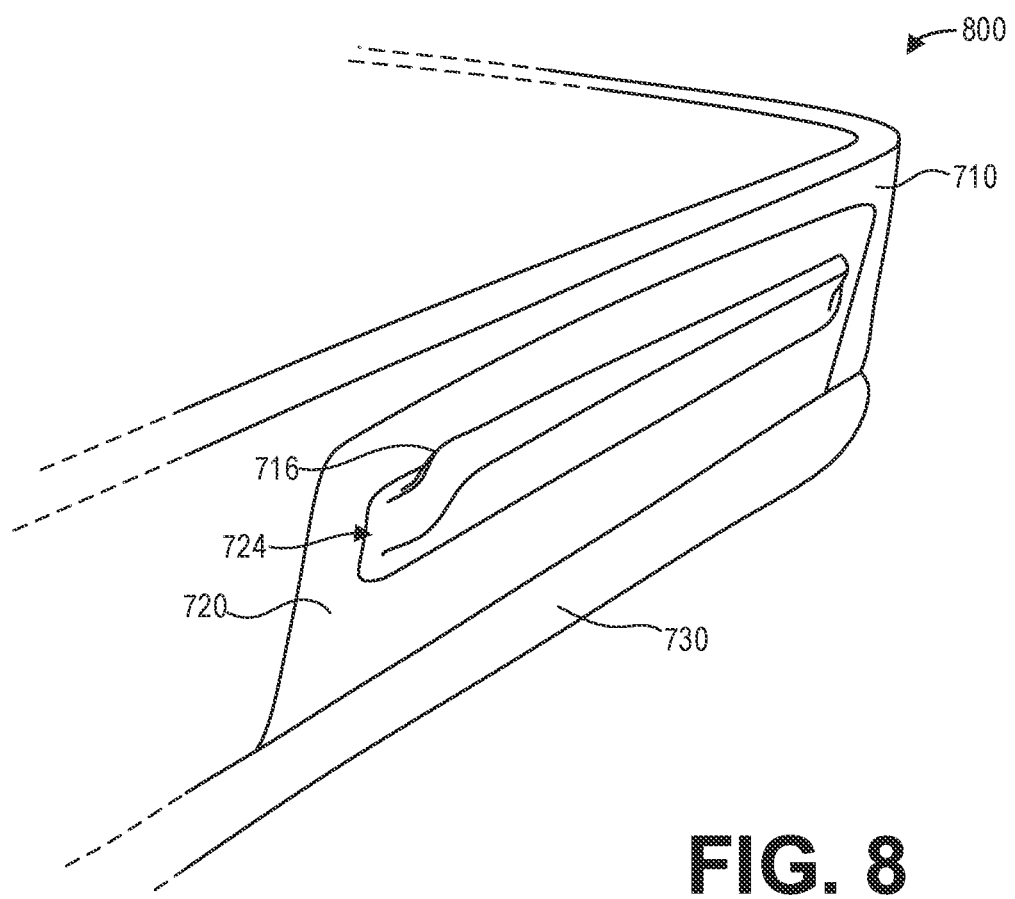
FIG. 8 shows another view of the scanning assembly of FIG. 7.
Figure 9:
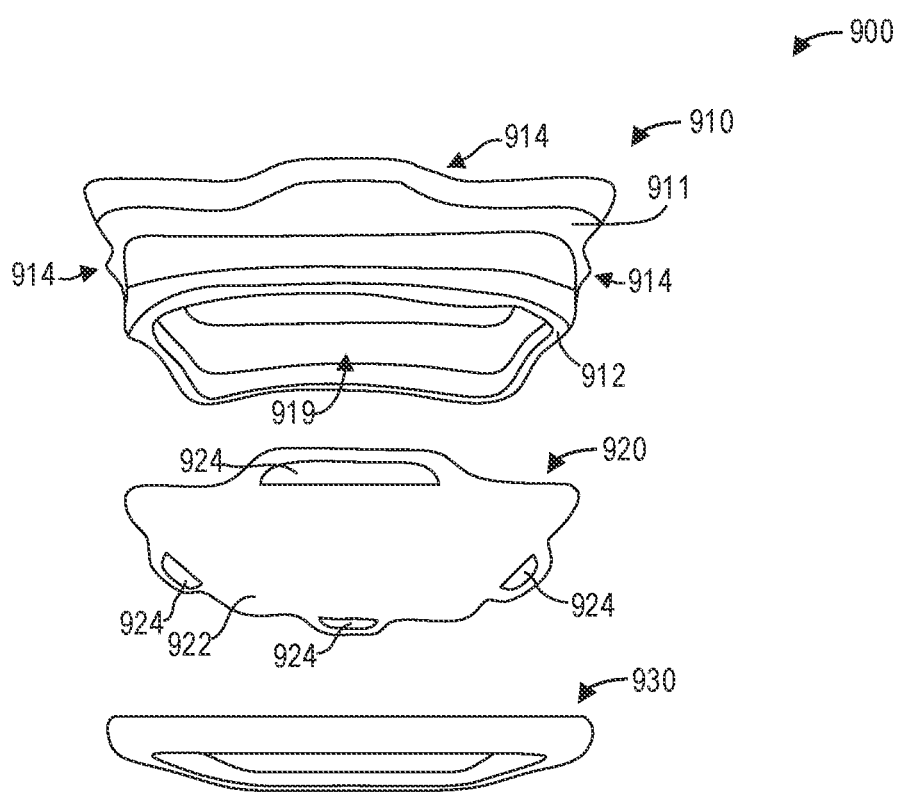
FIG. 9 shows a perspective exploded view of a scanning assembly for a scanning apparatus according to an embodiment.

The following description relates to various embodiments of a breast ultrasound imaging apparatus. FIGS. 1-3 illustrate an example full-field breast ultrasound (FFBU) scanning apparatus. The FFBU scanning apparatus includes a padding, as depicted in FIG. 4, to improve the comfort of a patient being scanned with the FFBU scanning apparatus. A membrane, such as the membrane depicted in FIG. 5, is directly and removably coupled to the scanning apparatus. The membrane may be secured to the scanning apparatus via a hinged locking ring, as depicted in FIG. 6. Alternatively, as depicted in FIGS. 7-9, the membrane may be directly coupled to the frame of the scanning apparatus while a locking ring secures the membrane.

In one example, a full-field breast ultrasound (FFBU) scanning apparatus, such as the FFBU scanning apparatus depicted in FIGS. 1 and 2, compresses a breast in a generally chestward or head-on direction and ultrasonically scans the breast. In another example, the FFBU scanning apparatus may compress a breast along planes such as the craniocaudal (CC) plane, the mediolateral oblique (MLO) plane, or the like. A compression/scanning assembly of the FFBU scanning apparatus may include an at least partially conformable, substantially taut membrane or film sheet, an ultrasound transducer, and a transducer translation mechanism. One side of the taut membrane or film sheet compresses the breast. The transducer translation mechanism maintains the ultrasound transducer in contact with the other side of the film sheet while translating the ultrasound transducer thereacross to scan the breast.

Typically, to maintain the transducer in contact with the film sheet and breast, a user of the transducer (such as a nurse, technician, or physician) physically applies a downward force on the transducer (e.g., in a direction toward the tissue to be scanned). In order to collect high-quality images, particularly of a dense tissue such as breast tissue, a considerably amount of force may be placed on the transducer to compress the tissue. Over time, the force applied by the user may decrease and/or may be applied unequally, resulting in degraded images. Further, this force may be uncomfortable or even painful for the patient; as discussed further herein, a padding may be provided to improve the comfort of the patient during a scan.

Although several examples herein are presented in the particular context of human breast ultrasound, it is to be appreciated that the present teachings are broadly applicable for facilitating ultrasound scanning of any externally accessible human or animal body part (e.g., abdomen, legs, feet, arms, neck, etc.). Moreover, although several examples herein are presented in the particular context of mechanized scanning (i.e., in which the ultrasound transducer is moved by a robot arm or other automated or semi-automated mechanism), it is to be appreciated that one or more aspects of the present teachings can be advantageously applied in a handheld scanning context.

FIG. 1 illustrates a perspective view of a full-field breast ultrasound (FFBU) scanning apparatus 102, hereinafter also referred to generally as scanning apparatus 102, according to an embodiment. Scanning apparatus 102 comprises a frame 104, an ultrasound processor housing 105 that contains an ultrasound processor, a movable and adjustable support arm 106 (e.g., adjustable arm) including a hinge joint 114, a compression/scanning assembly 108 connected to a first end 120 of the adjustable arm 106 via a ball-and-socket connector (e.g., ball joint) 112, and a display 110 connected to the frame 104. The display 110 is coupled to the frame 104 at an interface where the adjustable arm 106 enters into the frame 104. As a result of being directly coupled to the frame 104 and not to the adjustable arm 106, the display 110 does not affect a weight of the adjustable arm 106 and a counterbalance mechanism of the adjustable arm 106. In one example, the display 110 is rotatable in a horizontal and lateral direction (e.g., rotatable around a central axis of the frame 104), but not vertically movable. In an alternate example, the display 110 may also be vertically movable. While FIG. 1 depicts the display 110 coupled to the frame 104, in other examples the display 110 may be coupled to a different component of the scanning apparatus 102, such as coupled to the ultrasound processor housing 105, or located remotely from the scanning apparatus 102.

In one embodiment, the adjustable arm 106 is configured and adapted such that the compression/scanning assembly 108 is either (i) neutrally buoyant in space, or (ii) has a light net downward weight (e.g., 1-2 kg) for breast compression, while allowing for easy user manipulation. In alternate embodiments, the adjustable arm 106 is configured such that the compression/scanning assembly 108 is neutrally buoyant in space during positioning the scanner on the patient's tissue. Then, after positioning the compression/scanning assembly 108, internal components of the scanning apparatus 102 may be adjusted to apply a desired downward weight for breast compression and increased image quality. In one example, the downward weight (e.g., force) may be in a range of 2-11 kg.

As introduced above, the adjustable arm 106 includes a hinge joint 114. The hinge joint 114 bisects the adjustable arm 106 into a first arm portion and a second arm portion. The first arm portion is coupled to the compression/scanning assembly 108 and the second arm portion is coupled to the frame 104. The hinge joint 114 allows the second arm portion to rotate relative to the second arm portion and the frame 104. For example, the hinge joint 114 allows the compression/scanning assembly 108 to translate laterally and horizontally, but not vertically, with respect to the second arm portion and the frame 104. In this way, the compression/scanning assembly 108 may rotate toward or away from the frame 104. However, the hinge joint 114 is configured to allow the entire adjustable arm 106 (e.g., the first arm portion and the second arm portion) to move vertically together as one piece (e.g., translate upwards and downwards with the frame 104).

The compression/scanning assembly 108 comprises an at least partially conformable membrane 118 in a substantially taut state for compressing a breast, the membrane 118 having a bottom surface contacting the breast while a transducer is swept across a top surface thereof to scan the breast. In one example, the membrane is a taut fabric sheet.

Optionally, the adjustable arm may comprise potentiometers (not shown) to allow position and orientation sensing for the compression/scanning assembly 108, or other types of position and orientation sensing (e.g., gyroscopic, magnetic, optical, radio frequency (RF)) can be used. Within ultrasound processor housing 105 may be provided a fully functional ultrasound engine for driving an ultrasound transducer and generating volumetric breast ultrasound data from the scans in conjunction with the associated position and orientation information. In some examples, the volumetric scan data may be transferred to another computer system for further processing using any of a variety of data transfer methods known in the art, or the volumetric scan data may be processed by the ultrasound engine. A general purpose computer/processor, which may be integrated with the ultrasound engine, may also be provided for general user interfacing and system control. The general purpose computer may be a self-contained stand-alone unit, or may be remotely controlled, configured, and/or monitored by a remote station connected across a network.

FIG. 2 is a block diagram 200 schematically illustrating various system components of the scanning apparatus 102, including the scanning assembly 108, display 110, and a scanning processor 210. Scanning processor 210 may be included within ultrasound processor housing 105 of the scanning apparatus 102 in one example. As illustrated in the embodiment of FIG. 2, the scanning assembly 108, display 110, and scanning processor 210 are separate components in communication with each other; however, in some embodiments, one or more of the components may be integrated (e.g., the display and scanning processor may be included in a single component).

Referring first to the scanning assembly 108, it comprises a transducer module 220 connected to a module receiver 230. The module receiver 230 may be positioned within a housing (attached to the arm 106 of the scanning apparatus, for example) that is configured to remain stationary during scanning, while the module receiver 230 is configured to translate with respect to the housing during scanning. In order to automatically translate with respect to the housing during scanning, the module receiver includes a motor 232 activated by the scanning processor 210, as explained below.

The transducer module 220 comprises a transducer array 222 of transducer elements, such as piezoelectric elements, that convert electrical energy into ultrasound waves and then detect the reflected ultrasound waves. The transducer module 220 is configured to be removably coupled with the module receiver 230 via a connection 234. The connection 234 may include complementary connectors on the transducer module and module receiver (e.g., a first connector on the transducer module that is configured to connect with a second connector on the module receiver) in order to establish both a mechanical connection and an electrical connection between the module receiver and the transducer module.

The transducer module 220 may further include a memory 224. Memory 224 may be a non-transitory memory configured to store various parameters of the transducer module 220, such as transducer usage data (e.g., number of scans performed, total amount of time spent scanning, etc.), as well as specification data of the transducer (e.g., number of transducer array elements, array geometry, etc.) and/or identifying information of the transducer module 220, such as a serial number of the transducer module. Memory 224 may include removable and/or permanent devices, and may include optical memory, semiconductor memory, and/or magnetic memory, among others. Memory 224 may include volatile, non-volatile, dynamic, static, read/write, read-only, random-access, sequential-access, and/or additional memory. In an example, memory 224 may include RAM. Additionally or alternatively, memory 224 may include EEPROM.

Memory 224 may store non-transitory instructions executable by a controller or processor, such as controller 226, to carry out one or more methods or routines as described herein below. Controller 226 may receive output from various sensors 228 of the transducer module 220 and trigger actuation of one or more actuators and/or communicate with one or more components in response to the sensor output. Sensors 228 may include one or more pressure sensors and/or one or more temperature sensors. During scanning, the pressure across the scanning assembly 108 may be measured by the pressure sensors, and if the pressure distribution across the transducer module is not equal, a user may be notified (via user interface 242 of display 110, for example) to reposition the scanning assembly 108. Further, in some embodiments, to initiate scanning, motor 232 may be activated via a signal from controller 226. However, in other embodiments, motor 232 may be activated via a signal from a separate scanning processor 210, explained below.

Scanning assembly 108 may be in communication with scanning processor 210, to send raw scanning data to an image processor, for example. Additionally, data stored in memory 224 and/or output from sensors 228 may be sent to scanning processor 210 in some examples. Further, various actions of the scanning assembly 108 (e.g., translation of the module receiver 230, activation of the transducer elements, etc.) may be initiated in response to signals from the scanning processor 210. Scanning assembly 108 may optionally communicate with display 110, in order to notify a user to reposition the scanning assembly, as explained above, or to receive information from a user (via user input 224), for example.

Turning now to scanning processor 210, it includes an image processor 212, storage 214, display output 216, and ultrasound engine 218. Ultrasound engine 218 may drive activation of the transducer elements of the transducer array 222 of transducer module 220 and, in some embodiments, may activate motor 232. Further, ultrasound engine 218 may receive raw image data (e.g., ultrasound echoes) from the scanning assembly 108. The raw image data may be sent to image processor 212 and/or to a remote processor (via a network, for example) and processed to form a displayable image of the tissue sample. It is to be understood that the image processor 212 may be included with the ultrasound engine 218 in some embodiments.

Information may be communicated from the ultrasound engine 218 and/or image processor 212 to a user of the scanning apparatus 102 via the display output 216 of the scanning processor 210. In one example, the user of the scanning apparatus may include an ultrasound technician, nurse, or physician such as a radiologist. For example, processed images of the scanned tissue may be sent to the display 110 via the display output 216. In another example, information relating to parameters of the scan, such as the progress of the scan, may be sent to the display 110 via the display output 216. The display 110 may include a user interface 242 configured to display images or other information to a user. Further, user interface 242 may be configured to receive input from a user (such as through user input 244) and send the input to the scanning processor 210. User input 244 may be a touch screen of the display 110 in one example. However, other types of user input mechanisms are possible, such as a mouse, keyboard, etc.

Scanning processor 210 may further include storage 214. Similar to memory 224, storage 214 may include removable and/or permanent devices, and may include optical memory, semiconductor memory, and/or magnetic memory, among others. Storage 214 may include volatile, non-volatile, dynamic, static, read/write, read-only, random-access, sequential-access, and/or additional memory. Storage 214 may store non-transitory instructions executable by a controller or processor, such as ultrasound engine 218 or image processor 212, to carry out one or more methods or routines as described herein below. Storage 214 may store raw image data received from the scanning assembly 108, processed image data received from image processor 212 or a remote processor, and/or additional information.

FIG. 3 shows a schematic 300 of an isometric view of the scanning assembly 108 coupled to the adjustable arm 106. The schematic 300 includes a coordinate system 302 including a vertical axis 304, horizontal axis 306, and a lateral axis 308.

The scanning assembly 108 includes a housing 310, the transducer module 220, and the module receiver 230. The housing 310 includes a frame 322 and a handle portion 324, the handle portion including two handles 312. The two handles 312 are opposite one another across a lateral axis of the scanning assembly 108, the lateral axis centered at the adjustable arm 106 and defined with respect to the lateral axis 308. The frame 322 is rectangular-shaped with an interior perimeter of the frame 322 defining an opening 314. The opening 314 provides a space (e.g., void volume) for translating the module receiver 230 and the transducer module 220 during a scanning procedure. In another example, the frame 322 may be another shape, such as square with a square-shaped opening 314. Additionally, the frame 322 has a thickness defined between the interior perimeter and an exterior perimeter of the frame 322.

The frame 322 includes four sets of side walls (e.g., the set including an interior side wall and an exterior side wall, the interior side walls defining the opening 314). Specifically, the frame 322 includes a front side wall 326 and a back side wall 328, the back side wall 328 directly coupled to the handle portion 324 of the housing 310 and the front side wall 326 opposite the back side wall 328 with respect to the horizontal axis 306. The frame 322 further includes a right side wall and a left side wall, the respective side walls opposite from one another and both in a plane defined by the vertical axis 304 and the lateral axis 308.

The frame 322 of the housing 310 further includes a top side and a bottom side, the top side and bottom side defined relative to the vertical axis 304. The top side faces the adjustable arm 106. A membrane 118 is disposed across the opening 314. More specifically, the membrane 118 is coupled to the bottom side of the frame 322. In one example, the membrane 118 is a membranous sheet maintained taut across the opening 314. The membrane 118 may be a flexible but non-stretchable material that is thin, water-resistant, durable, highly acoustically transparent, chemically resistant, and/or biocompatible. As discussed above, the bottom surface of the membrane 118 may contact a tissue (e.g., such as a breast) during scanning and a top surface of the membrane 118 may at least partially contact the transducer module 220 during scanning. As shown in FIG. 3, the membrane 118 is permanently coupled to a hard-shell clamping portion 119 around a perimeter of the membrane 118. The clamping portion 119 couples to the bottom side of the frame 322. In one example, the clamping portion 119 may snap to a lip on the bottom side of the frame 322 of the housing 310 such that the membrane 118 does not become uncoupled during scanning but is still removably coupled to the frame 322. As discussed further herein with respect to FIGS. 4-9, the membrane 118 may not be permanently coupled to a hard-shell clamping portion 119, and thus the membrane 118 may not couple to the frame 322 via the hard-shell clamping portion 119. Instead, the membrane 118 may be directly and removably coupled to the frame 322.

The handle portion 324 of the housing 310 includes two handles 312 for moving the scanning assembly 108 in space and positioning the scanning assembly 108 on a tissue (e.g., on a patient). In alternate embodiments, the housing 310 may not include handles 312. In one example, the handles 312 may be formed as one piece with the frame 322 of the housing 310. In another example, the handles 312 and the frame 322 may be formed separately and then mechanically coupled together to form the entire housing 310 of the scanning assembly 108.

As shown in FIG. 3, the scanning assembly 108 is coupled to the adjustable arm 106 through a ball joint 112 (e.g., ball-and-socket connector). Specifically, a top, domed portion of the handle portion 324 is coupled to the ball joint 112. The top portion of the handle portion 324 includes a concave depression forming a socket which a ball of the ball joint 112 fits into. The ball joint 112 is movable in multiple directions. For example, the ball joint 112 provides rotational movement of the scanning assembly relative to the adjustable arm 106. The ball joint 112 includes a locking mechanism for locking the ball joint 112 in place and thereby maintaining the scanning assembly 108 stationary relative to the adjustable arm 106.

Additionally, as shown in FIG. 3, the handles 312 of the handle portion 324 include buttons for controlling scanning and adjusting the scanning assembly 108. Specifically, a first handle of the handles 312 includes a first weight adjustment button 316 and a second weight adjustment button 318. The first weight adjustment button 316 may decrease a load applied to the scanning assembly 108 from the adjustable arm 106. The second weight adjustment button 318 may increase the load applied to the scanning assembly 108 from the adjustable arm 106. Increasing the load applied to the scanning assembly 108 may increase an amount of pressure and compression applied to the tissue on which the scanning assembly 108 is placed. Further, increasing the load applied to the scanning assembly increases the effective weight of the scanning assembly on the tissue to be scanned. In one example, increasing the load may compress the tissue, such as a breast, of a patient. In this way, varying amounts of pressure (e.g., load) may be applied consistently with the scanning assembly 108 during scanning in order to obtain a quality image with the transducer module 220.

Before a scanning procedure, a user (e.g., ultrasound technician or physician) may position the scanning assembly 108 on a patient or tissue. Once the scanning assembly 108 is positioned correctly, the user may adjust the weight of the scanning assembly 108 on the patient (e.g., adjust the amount of compression) using the first weight adjustment button 316 and/or the second weight adjustment button 318. A user may then initiate a scanning procedure with additional controls on the handle portion 324 of the housing 310. For example, as shown in FIG. 3, a second handle of the handles 312 includes two additional buttons 330 (not individually shown). The two additional buttons 330 may include a first button to initiate scanning (e.g., once the scanning assembly has been placed on the tissue/patient and the amount of compression has been selected) and a second button to stop scanning. In one example, upon selecting the first button, the ball joint 112 may lock, thereby stopping lateral and horizontal movement of the scanning assembly 108.

The module receiver 230 is positioned within the housing 310. Specifically, the module receiver 230 is mechanically coupled to a first end of the housing 310 at the back side wall 328 of the frame 322, the first end closer to the adjustable arm 106 than a second end of the housing 310. The second end of the housing 310 is at the front side wall 326 of the frame 322. In one example, the module receiver 230 is coupled to the first end via a protrusion of the module receiver 230, the protrusion coupled to a motor 230, the protrusion coupled to a motor (e.g., motor 232 described with reference to FIG. 2 above) of the module receiver 230.

As described above, the housing 310 is configured to remain stationary during scanning. In other words, upon adjusting a weight applied to the scanning assembly 108 through the adjustable arm 106 and then locking the ball joint 112, the housing 310 may remain in a stationary position without translating in the horizontal or lateral directions. However, the housing 310 may still translate vertically with vertical movement of the adjustable arm 106.

Conversely, the module receiver 230 is configured to translate with respect to the housing 310 during scanning. As shown in FIG. 3, the module receiver 230 translates horizontally, along the horizontal axis 306, with respect to the housing 310. The motor of the module receiver 230 may slide the module receiver 230 along a top surface of the first end of the housing 310.

The transducer module 220 is removably coupled with the module receiver 230. As a result, during scanning, the transducer module 220 translates horizontally with the module receiver 230. During scanning, transducer module 220 sweeps horizontally across the breast under motor control of the module receiver 230 while a contact surface of the transducer module 220 is in contact with the membrane 118. The transducer module 220 and the module receiver 230 are coupled together at a module interface 320. The module receiver 230 has a width 332 which is the same as a width of the transducer module 220. In alternate embodiments, the width 332 of the module receiver may not be the same as the width of the transducer module 220. In some embodiments, the module interface 320 includes a connection 234 between the transducer module 220 and the module receiver 230, the connection 234 including a mechanical and electrical connection.

As mentioned above, in previous embodiments of the scanning apparatus 108, the membrane 118 is typically coupled to a hard-shell clamping portion 119 around a perimeter of the membrane 118. The hard-shell clamping portion 119 typically comprises a rigid acrylonitrile butadiene styrene (ABS) plastic and is permanently coupled to the membrane 118. The rigidity of the clamping portion 119 of the membrane 118 can cause discomfort during use, especially for patients with a small body type. Further, the membrane 118 is intended for single use, but the permanent coupling of the clamping portion 119 to the membrane 118 increases the cost of the membrane 118 and thus some users may re-use the membrane 118 for different patients to reduce the cost.

As discussed further herein, various embodiments of a scanning assembly 108 and a membrane 118 are provided to improve the comfort for the patient as well as reduce the cost of the membrane 118. In particular, the various embodiments include a membrane 118 comprising a polyester mesh membrane that is not permanently coupled to a rigid ABS frame such as the clamping portion 119.

FIG. 4 shows a perspective view of a bottom side 400 of a scanning assembly of a scanning apparatus according to an embodiment. In particular, the bottom side 400 may comprise the bottom side of the frame 322 of the scanning apparatus 108 described hereinabove.

The bottom side 400 includes a slot or recess 405 adapted to receive a perimeter of a membrane. To that end, the recess 405 extends around the perimeter of the bottom side 400 of the scanning apparatus. Further, the recess 405 may be sized to securely receive the membrane.

The bottom side 400 further includes a padding 410 extending around the bottom surface of the bottom side 400, as depicted. The padding 410 may comprise a soft rubber, a firm foam, or a polyurethane material with a hardness value selected to increase the comfort of a patient. For example, a hardness value for the padding 410 may range from medium soft to medium hard. More specifically, the durometer value of the padding 410 may range from 30 to 50 Shore A, as an illustrative and non-limiting example. The padding 410 cushions the tissue of the patient from the hard surfaces of the scanning apparatus during an ultrasound scan, thereby improving the comfort for the patient when the patient's tissue is being compressed against the scanning apparatus.

As an illustrative example, FIG. 5 shows a perspective view of an example membrane 500 that may be removably coupled to the bottom side 400 according to an embodiment. In some examples, the membrane 500 comprises a polyester mesh weave. The membrane 500 includes a region 502 of the polyester mesh material substantially shaped to cover the bottom side 400 of the scanning apparatus. The thickness of the region 502 may range from 0.003 mm to 0.008 mm, in some examples. The membrane 500 further comprises a ring 505 extending around the perimeter of the region 502. The ring 505 may be formed from the material as the region 502, and thus in some examples the ring 505 may comprise a polyester mesh weave. The thickness or diameter of the ring 505 may be approximately 0.250 mm, in some examples.

Referring now to both FIGS. 4 and 5, the membrane 500 may be stretched taut over the opening 414 of the bottom side 400 and the padding 410 of the bottom side 400 that extends at least partially around the perimeter of the bottom side 400. The ring 505 is sized and shaped to fit securely into the recess 405 of the bottom side 400. By providing a membrane 500 that is not permanently fixed to a hard-shelled frame, the manufacturing cost of the membrane 500 is substantially reduced, thereby improving the disposability of the membrane 500. Furthermore, the comfort of the patient is increased because the tissue of the patient is not compressed against a hard-shelled frame.

In some examples, the membrane 500 may be securely fixed to the bottom side 400 of the scanning apparatus by inserting the ring 505 into the recess 405. In other examples, as discussed herein below, a magnetic lock ring and/or a tray may be used to further secure the membrane 500 to the bottom side 400.

As an example, FIG. 6 shows a cross-sectional view of a scanning assembly 600 of a scanning apparatus according to an embodiment. The scanning assembly 600 includes a frame 602, which may comprise the frame 322 described hereinabove with regard to FIG. 3. The frame 602 includes a top side 604 and a bottom side 606, as discussed hereinabove. The frame 602 includes a recess 608 extending around the perimeter of the frame 602 and adapted to receive the ring 505 of the membrane 500. As depicted, the recess 608 may be formed in the bottom side 606 of the scanning assembly 600. To that end, the recess 608 may comprise the recess 405 described hereinabove with regard to FIG. 4. The frame 602 further includes a padding 612 that extends around an opening 614 in the bottom side 606.

A membrane (not shown) such as membrane 500 described hereinabove may be stretched taut over the opening 614 in the bottom side 606, and the perimeter or ring of the membrane may be inserted into the recess 608 of the frame 602.

The scanning apparatus 600 may further include a hinged locking ring 620 to secure the membrane. For example, after stretching the membrane over the opening 614 and the padding 612 and inserting the ring of the membrane into the recess 608, the hinged locking ring 620 may be closed to secure the membrane. For example, the hinged locking ring 620 may rotate, via a hinge 622 that couples the hinged locking ring 620 to the scan head 602, in the direction 630 towards the bottom side 606 of the frame 602. The hinged locking ring 620 may clip to the frame 602 to secure the hinged locking ring 620 in a closed position, in some examples. In other examples, one or more of the bottom side 606 of the frame 602 and the hinged locking ring 620 may be magnetized such that the hinged locking ring 620 remains in the closed position. Further, the hinged locking ring 620 includes an opening 626 that corresponds to the opening 614 of the bottom side 606 of the frame 602.

In some examples, an optional tensioning mechanism 624 increases the tension of the membrane to a desired tension. In some examples, the tensioning mechanism 624 enables a variable tension of the membrane. A variable tension of the membrane may be adjusted to provide adequate tension based on a size and/or density of the tissue to be examined. Although the tensioning mechanism 624 is depicted as being integrated into the hinged locking ring 620, it should be appreciated that in some examples the tensioning mechanism 624 may be fixed to the lower portion 606 of the frame 602. The tensioning mechanism 624 may comprise a tensioning bar, as an illustrative and non-limiting example.

As another example, FIG. 7 shows a perspective exploded view of a scanning assembly 700 for a scanning apparatus according to an embodiment. The scanning assembly 700 includes a housing 710, a membrane 720 that may be removably coupled to the housing 710, and a locking ring 730 that secures the membrane 720 to the housing 710.

The housing 710 comprises a frame 712 and a handle 714. As depicted, the handle 714 extends from the frame 712 over a top side of the frame 712. It should be appreciated that although a single handle 714 is depicted, other configurations of a housing for the scanning assembly 700 may be used, such as the housing 310 of the scanning assembly 108 described hereinabove with regard to FIG. 3.

The housing 710 further includes two or more hooks or protrusions 716 that extend outward from the sides of the frame 712. For example, a first protrusion 716 may extend from a first side of the frame 712, while a second protrusion (not shown) may extend from a second side of the frame 712 opposite the first side.

Further, as depicted, the housing 710 includes a padding 717 provided along a perimeter of the opening 718 in the bottom side of the housing 710. The padding 717 may comprise the padding 410 described hereinabove and thus may provide improved comfort to the patient during a scan.

The membrane 720 may comprise a polyester mesh weave and may not include a hard-shell plastic frame. Instead, the membrane 720 includes a plurality of openings, such as opening 722 and opening 724. The membrane 720 may be secured to the housing 710 by stretching the membrane 720 over the opening 718 of the housing 710 and fastening the opening 724 over the first protrusion 716 and the opening 722 over the second protrusion.

Once the membrane 720 is coupled to the housing 710, the locking ring 730 may be coupled to the housing 710 to secure the membrane 720 in place. In one example, the locking ring 730 may be adapted to clip mechanically to the housing 710. In another example, at least one of a portion of the housing 710 and the locking ring 730 may be magnetized such that the locking ring 730 is magnetically coupled to the housing 710.

To illustrate how the housing 710, the membrane 720, and the locking ring 730 may be coupled together, FIG. 8 shows another view 800 of the scanning assembly 700 wherein the membrane 720 and the locking ring 730 are coupled to the housing 710. As depicted, the protrusion 716 extends outward from the side of the housing 710 and through the opening 724 of the membrane 720. Additionally, the locking ring 730 couples to the housing 710, thereby securing the membrane 720 in place. The locking ring 730 includes an opening 734 so that the outer face of the membrane 720 may still contact the tissue of the patient being scanned. Further, the locking ring 730 may be formed to at least partially enclose the exterior of the padding 717, such that the interior of the locking ring 730 and the exterior of the padding 717 are in face-sharing contact. In this way, when compressing the scanning apparatus 700 against the tissue of the patient, the body of the patient presses against the padding 717 instead of the hard surface of the locking ring 730 or the housing 710.

Thus, in some examples, a membrane for a scanning apparatus may be removably coupled to the scanning apparatus via a plurality of protrusions. Further, although not illustrated in FIGS. 7 and 8, in some examples one or more of the plurality of protrusions may be adapted to vary the tension of the membrane 720. For example, the position of the protrusion 716 on the side of the housing 710 may be adjustable in the vertical direction (e.g., as indicated by the vertical axis 304 in FIG. 3). In such an example, increasing the vertical position of the protrusion 716 increases the tension of the membrane 720, while decreasing the vertical position of the protrusion 716 reduces the tension of the membrane 720.

As another illustrative example, FIG. 9 shows a perspective exploded view of a scanning assembly 900 for a scanning apparatus according to an embodiment. For simplicity, only the bottom side 910 of the scanning assembly 900 is depicted. The frame 911 includes a plurality of protrusions 914 that extend outward from the sides of the frame 911. The frame 911 also includes a padding 912 similar to the paddings described hereinabove. The membrane 920 comprises a polyester mesh weave material 922 as described hereinabove, as well as a plurality of openings 924 in the polyester mesh weave material 922. Each opening 924 corresponds to a protrusion 914 of the frame 911. The membrane 920 is stretched over the opening 919 of the bottom face of the frame 911 as well as the padding 912, and the openings 924 of the membrane 920 are coupled to corresponding protrusions of the protrusions 914. Specifically, the protrusions 914 pass through the openings 924 of the membrane 920. To further secure the membrane 920 to the frame 911, the locking ring 930 is coupled to the frame 911. That is, once the membrane 920 is coupled to the frame 911, the locking ring 930 may be fixed to the frame 911. The locking ring 930 may be mechanically or magnetically coupled to the frame 911, as described hereinabove.

Thus, various embodiments of a breast ultrasound scanning apparatus are provided. In one embodiment, a system comprises an imaging assembly comprising an ultrasound transducer, a frame housing the imaging assembly, and a membrane directly and removably coupled to the frame.

In a first example of the system, the membrane is stretched taut across an opening in a bottom side of the frame, and a top surface of the membrane is at least partially in contact with the ultrasound transducer during an ultrasound scan. In a second example of the system optionally including the first example, the system further comprises a padding extending around the opening in the bottom side of the frame, the padding further extending at least partially outwards from the bottom side of the frame. In a third example of the system optionally including one or more of the first and second examples, the membrane is directly and removably coupled to at least a first side and a second side of the frame, the first side opposite from the second side. In a fourth example of the system optionally including one or more of the first through third examples, the frame includes at least two protrusions extending outward from the first side and the second side, and the at least two protrusions extend through corresponding openings formed in the membrane. In a fifth example of the system optionally including one or more of the first through fourth examples, the membrane is directly and removably coupled to a recess extending around an outer perimeter of the frame. In a sixth example of the system optionally including one or more of the first through fifth examples, the system further comprises a locking ring coupled to the frame to secure the membrane. In a seventh example of the system optionally including one or more of the first through sixth examples, the locking ring is coupled to the frame via a hinge. In an eighth example of the system optionally including one or more of the firs through seventh examples, the locking ring is removably and mechanically coupled to the frame. In a ninth example of the system optionally including one or more of the first through eighth examples, the locking ring is removably and magnetically coupled to the frame. In a tenth example of the system optionally including one or more of the first through the ninth examples, the membrane comprises an at least partially conformable polyester material. In an eleventh example of the system optionally including one or more of the first through the tenth examples, the system further comprises a tensioning mechanism adapted to vary a tautness of the membrane.

In another embodiment, an apparatus comprises an imaging assembly comprising an ultrasound transducer, a frame housing the imaging assembly, a padding fixed to the frame around a perimeter of an opening in a bottom side of the frame, and a membrane directly and removably coupled to the frame, the membrane stretched taught across the opening and over the padding, wherein, during an ultrasound scan with the ultrasound transducer of tissue of a patient, the tissue is compressed against the padding and a bottom surface of the membrane while the ultrasound transducer is at least partially in contact with a top surface of the membrane.

In a first example of the apparatus, the padding comprises an elastomeric material with a durometer value ranging from 30 to 50 Shore A. In a second example of the apparatus optionally including the first example, the membrane comprises an at least partially conformable polyester material. In a third example of the apparatus optionally including one or more of the first and the second examples, the membrane includes a ring formed from the at least partially conformable polyester material and positioned along a perimeter of the membrane, wherein the ring is inserted into a recess extending around an outer perimeter of the frame to directly and removably couple the membrane to the frame. In a fourth example of the apparatus optionally including one or more of the first through the third examples, the membrane includes at least two openings and the frame includes at least two protrusions extending away from the frame, wherein the membrane is directly and removably coupled to the frame by inserting the at least two protrusions through the at least two openings.

In yet another embodiment, a membrane for an ultrasound scanning apparatus, comprises an at least partially conformable polyester material shaped as a sheet that when directly coupled to a frame of the ultrasound scanning apparatus is substantially taut across an opening in the frame.

In a first example of the membrane, the membrane includes two or more openings through which protrusions extending outward from the frame are inserted when the membrane is directly coupled to the frame. In a second example of the membrane, the membrane further comprises a ring along a perimeter of the sheet formed from the at least partially conformable polyester material, wherein a diameter of the ring is greater than a thickness of the sheet, and wherein the ring is inserted into a recess of the frame when the membrane is directly coupled to the frame.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
   an imaging assembly comprising an ultrasound transducer;
   a frame housing the imaging assembly;
   a padding fixed to the frame around a perimeter of an opening in a bottom side of the frame, the padding extending at least partially outwards from the bottom side of the frame; and
   a membrane directly and removably coupled to the frame, the membrane stretched taut across the opening and over the padding when coupled to the frame;
   wherein, during an ultrasound scan with the ultrasound transducer of tissue of a patient, the padding is not in direct contact with the tissue of the patient and a bottom surface of the membrane is in contact with the tissue of the patient.

2. The system of claim 1, wherein a top surface of the membrane is at least partially in contact with the ultrasound transducer during the ultrasound scan.

3. The system of claim 1, wherein the membrane is directly and removably coupled to at least a first side and a second side of the frame, the first side opposite from the second side.

4. The system of claim 3, wherein the frame includes at least two protrusions extending outward from the first side and the second side, and wherein the at least two protrusions extend through corresponding openings formed in the membrane.

5. The system of claim 1, wherein the membrane is directly and removably coupled to a recess extending around an outer perimeter of the frame.

6. The system of claim 1, further comprising a locking ring coupled to the frame to secure the membrane.

7. The system of claim 6, wherein the locking ring is coupled to the frame via a hinge.

8. The system of claim 6, wherein the locking ring is removably and mechanically coupled to the frame.

9. The system of claim 6, wherein the locking ring is removably and magnetically coupled to the frame.

10. The system of claim 6, wherein the membrane comprises an at least partially conformable polyester material.

11. The system of claim 1, further comprising a tensioning mechanism adapted to vary a tautness of the membrane.

12. An apparatus, comprising:
    an imaging assembly comprising an ultrasound transducer;
    a frame housing the imaging assembly;
    a padding fixed to the frame around a perimeter of an opening in a bottom side of the frame; and
    a membrane directly and removably coupled to the frame, the membrane stretched taut across the opening and over the padding;
    wherein, during an ultrasound scan with the ultrasound transducer of tissue of a patient, the tissue is compressed against the padding and a bottom surface of the membrane while the ultrasound transducer is at least partially in contact with a top surface of the membrane and the padding is not in direct contact with the tissue of the patient.

13. The apparatus of claim 12, wherein the padding comprises an elastomeric material with a durometer value ranging from 30 to 50 Shore A.

14. The apparatus of claim 12, wherein the membrane comprises an at least partially conformable polyester material.

15. The apparatus of claim 14, wherein the membrane includes a ring formed from the at least partially conformable polyester material and positioned along a perimeter of the membrane, wherein the ring is inserted into a recess extending around an outer perimeter of the frame to directly and removably couple the membrane to the frame.

16. The apparatus of claim 12, wherein the membrane includes at least two openings and the frame includes at least two protrusions extending away from the frame, wherein the membrane is directly and removably coupled to the frame by inserting the at least two protrusions through the at least two openings.

* * * * *